US00PP31017P2

(12) United States Plant Patent
Head

(10) Patent No.: US PP31,017 P2
(45) Date of Patent: Nov. 5, 2019

(54) ***GARDENIA* PLANT NAMED 'WAH-SP'**

(50) Latin Name: *Gardenia jasminoides*
Varietal Denomination: WAH-SP

(71) Applicant: Southern Plant Group, LLC, Marietta, GA (US)

(72) Inventor: William A. Head, Walhalla, SC (US)

(73) Assignee: SOUTHERN PLANT GROUP, LLC, Marietta, GA (US)

( * ) Notice: Subject to any disclaimer, the term of this patent is extended or adjusted under 35 U.S.C. 154(b) by 0 days.

(21) Appl. No.: 16/350,616

(22) Filed: Dec. 11, 2018

(51) Int. Cl.
*A01H 5/02* (2018.01)
*A01H 6/76* (2018.01)

(52) U.S. Cl.
USPC ..... Plt./255

(58) Field of Classification Search
USPC ..... Plt./226, 255
See application file for complete search history.

*Primary Examiner* — Susan McCormick Ewoldt
*Assistant Examiner* — Karen M Redden
(74) *Attorney, Agent, or Firm* — Buchanan Ingersoll & Rooney PC

(57) ABSTRACT

A new and distinct variety of *gardenia* plant, referred to by its cultivar name, 'WAH-SP', is provided which forms double, medium sized, fragrant, white colored inflorescences. Attractive, glossy, dark green colored foliage is formed, which contrasts beautifully with the blossoms. The vegetation is moderately vigorous and the growth habit is wide and low. The new variety is well suited for proving attractive ornamentation in the landscape.

2 Drawing Sheets

Botanical/commercial classification:
Latin name—*Gardenia jasminoides.*
Common name—*Gardenia* Plant.
Varietal denomination: 'WAH-SP'.

SUMMARY OF THE INVENTION

The new variety of *Gardenia jasminoides Gardenia* plant was created in a controlled breeding program during the spring of 2006 at Seneca, S.C., U.S.A., by open pollination in the hope that they would contribute the desired characteristics. The female parent (i.e., the seed parent) was the 'Daisy' variety (non-patented). The male parent (i.e., the pollen parent) is unknown.

The parentage of the new variety can be summarized as follows:

'Daisy' x unknown

The new cultivar was discovered and selected as a single flowering plant within the progeny of the above-stated open-pollination during the summer of 2008 in a controlled environment at Seneca, S.C. Selective study resulted in the identification of a single plant of the new variety.

It was found that the new variety of *Gardenia* plant of the present invention possesses the following combination of characteristics:

(a) forms attractive, fragrant, medium-sized double, white-colored inflorescences,
(b) exhibits glossy, dark green colored foliage; and
(c) provides moderately vigorous vegetation, with wide and low growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Daisy' variety (i.e., the seed parent) displays upright to mounded growth habit and exhibits single inflorescences, whereas the new variety exhibits wide and low growth habit and double inflorescence. Moreover, the new variety can be readily distinguished from other similar non-parental varieties. For example, the 'Radicans' variety (not patented) displays smaller flower size and are less cold hardy compared to the new variety.

The new variety has been found to undergo asexual propagation at Seneca, S.C. and Hickory, N.C. by softwood cuttings since the summer of 2010. Asexual propagation by softwood cuttings in Seneca, S.C. and Hickory, N.C. has shown that the characteristics of the new variety are stable and are strictly transmissible by such asexual propagation from one generation to another. Accordingly, the new variety undergoes asexual propagation in a true-to-type manner.

The new variety has been named 'WAH-SP'.

BRIEF DESCRIPTION OF THE PHOTOGRAPHS

The accompanying photographs shows as nearly true as it is reasonably possible to make the same, in color illustrations of this character, typical specimens of the new variety. The *gardenia* plants of the new variety were approximately one year of age and were observed while growing outdoors at Cochranville, Pa., U.S.A. in 3-gallon containers.

Figure 1:
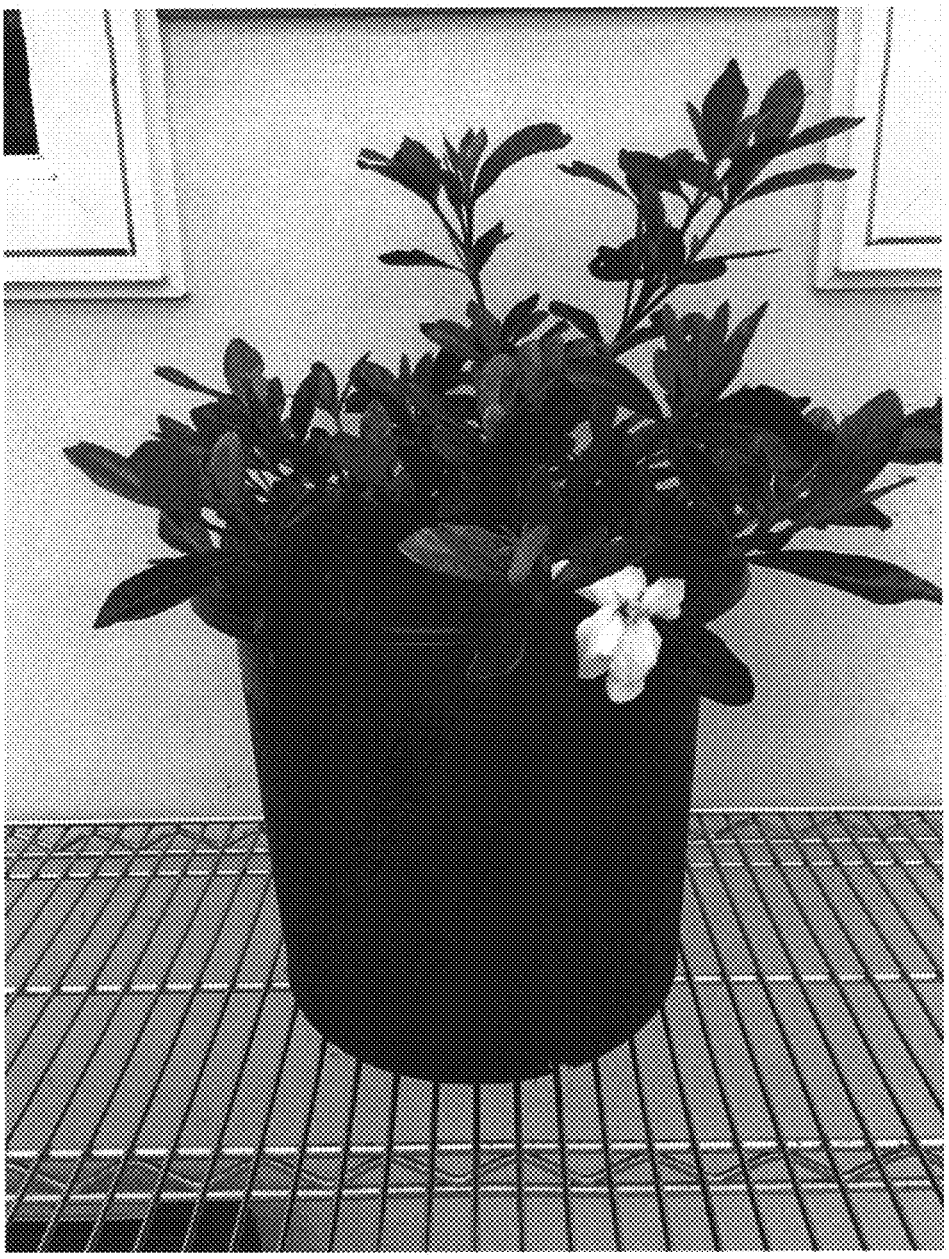
Figure 2:
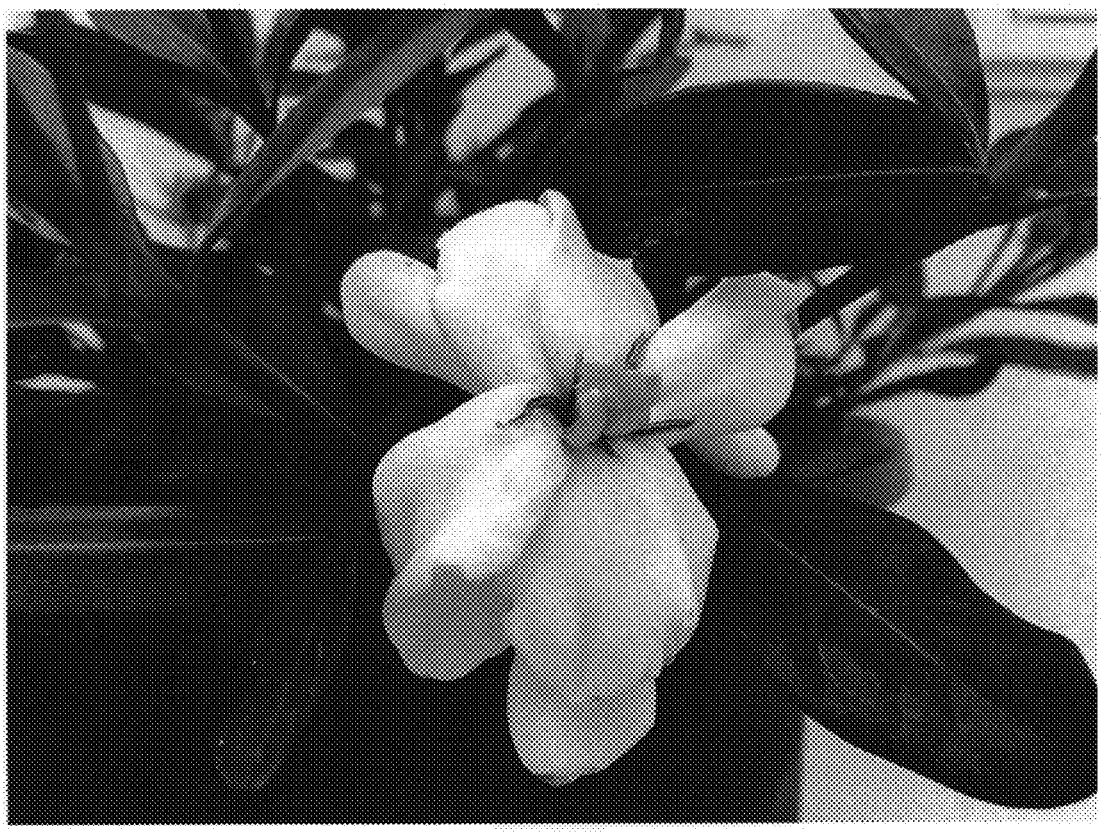

FIG. 1—illustrates a specimen the plant—side view.
FIG. 2—illustrates a specimen of a flower.

DETAILED BOTANICAL DESCRIPTION

The chart used in the identification of the colors is that of The Royal Horticultural Society (R.H.S. Colour Chart, 2015 edition), London, England. The terminology which precedes reference to the chart has been added to indicate the corresponding color in more common terms. The description is based on the observation of specimens of the new variety during August 2018 under natural light conditions at Cochranville, Pa., U.S.A. Numerical values represent averages of typical plants.

Class: *Gardenia* Plant.

Plant:

*Habit*.—Wide and low.

*Height*.—Approximately 30.0 cm on average from soil level to top of plant plane.

*Width*.—Approximately 45.0 cm on average.

Branches:

*Habit*.—Feely branching; pinching enhances branching.

*Quantity of lateral branches per plant*.—Approximately 8 main branches.

*Strength*.—Strong.

*Color*.—Mature stems: commonly near Group 203B.

*Length*.—Approximately 15.0 cm to 20.0 cm on average.

*Diameter*.—Approximately 5.0 mm on average.

*Central internode*.—Length is approximately 4.0 cm on average.

*Texture*.—Smooth.

Foliage:

*General appearance*.—Dark green with a glossy aspect.

*Fragrance*.—None detected.

*Form*.—Simple.

*Arrangement*.—Opposite.

*Leaves*.—Length: approximately 6.5 cm on average of mature leaves. Width: approximately 1.8 cm on average of mature leaves. Shape: elliptic; apex is acute; base is cuneate. Margin: entire. Venation pattern: pinnate. Texture of upper and lower surfaces: glabrous, with very glossy upper surface.

*Young foliage*.—Upper surface color: commonly near Green Group 141A with indistinguishable venation. Lower surface color: commonly near Green Group 143B with indistinguishable venation.

*Mature foliage*.—Upper surface color: commonly near Green Group 139A with venation commonly near Green Group 139B. Lower surface color commonly near Green Group 139B with venation commonly near Green Group 139C.

*Petiole*.—Length: approximately 2.0 mm on average. Diameter: approximately 2.0 mm on average. Texture: glabrous. Color: commonly near Yellow-Green Group 144A.

Inflorescence:

*Flower*.—Type: double, self-cleaning. Quantity per plant: approximately 2 open at a time. Fragrance: strong, pleasantly sweet. Aspect: upward to outward.

*Bud just before opening*.—Shape: oblong. Length: approximately 4.5 cm on average. Width: approximately 1.3 cm on average. Color: commonly near Yellow-Green 144A.

*Corolla*.—Shape: rotate. Depth: approximately 4.5 cm on average. Diameter: approximately 7.0 cm on average.

*Petals*.—Quantity per flower: approximately 12. Shape: obovate; apex is rounded; base is truncate. Margin: entire. Length: approximately 2.3 cm on average. Width: approximately 1.8 cm on average. Texture of upper and lower surfaces: glabrous. Color of upper and lower surfaces when fully open: commonly near White Group NN155C.

*Calyx*.—Shape: star-shaped. Depth: approximately 2.5 cm on average. Diameter: approximately 9.0 mm on average.

*Sepals*.—Quantity: commonly 6 on average. Shape: narrowly lanceolate; apex is acute; base is fused. Margin: entire. Length: approximately 2.2 cm on average. Width: approximately 2.0 mm on average. Texture of upper surface: glabrous. Texture of lower surface: glabrous. Color of upper and lower surfaces: commonly near Yellow-Green Group 144A.

*Peduncle*.—Strength: strong. Shape: rounded. Aspect: erect to about 45° from branch axis. Length: approximately 1.5 cm on average. Diameter: approximately 3.0 mm on average. Texture: glabrous. Color: commonly near Yellow-Green Group 144A.

*Stamen*.—Quantity: approximately 6 per flower. Length: approximately 1.2 cm on average.

*Anther*.—Shape: narrow oblong, dorsifixed. Length: approximately 1.2 cm on average. Color: commonly near Greyed-Yellow Group 161A.

*Pollen*.—Amount is moderate and color is commonly near Yellow-Orange Group 14C.

*Pistils*.—Quantity: commonly 1 per flower irregularly divided into three to five segments. Length: approximately 4.5 cm on average.

*Stigma*.—Shape: irregularly elliptic. Color: commonly near Yellow Group 6C.

*Style*.—Length: approximately 2.6 cm on average. Color: commonly near Yellow Group 4D.

*Ovary*.—Length: approximately 3.0 mm on average. Color: commonly near Yellow Group 3C.

*Seeds/fruits*.—None observed.

Development:

*Commercial crop time*.—Approximately one year from a rooted cutting to finish in a 3-gallon container.

*Vegetation*.—Moderately vigorous.

*Hardiness*.—USDA Zone 7 (0° F. to 10° F.).

*Flowering season*.—Flowers in spring with intermittent flowering in fall.

*Lastingness*.—Approximately one week of individual inflorescence on the plant.

*Resistance to disease*.—Resistance to pathogens and pests common to *Gardenia* plants has not been observed.

The new 'WAH-SP' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of *gardenia* plant characterized by the following combination of characteristics:

(a) forms attractive, fragrant, medium-sized double, white-colored inflorescences, (b) exhibits glossy, dark green colored foliage; and (c) provides moderately vigorous vegetation, with wide and low growth habit;

substantially as herein shown and described.

* * * * *